United States Patent [19]

Sih

[11] 4,289,904
[45] * Sep. 15, 1981

[54] 19-HYDROXY-6A-CARBA-PGI$_2$ SULFONYLAMIDES

[75] Inventor: John C. Sih, Portage, Mich.

[73] Assignee: The Upjohn Company, Kalamazoo, Mich.

[*] Notice: The portion of the term of this patent subsequent to Jul. 28, 1998, has been disclaimed.

[21] Appl. No.: 126,467

[22] Filed: Mar. 3, 1980

Related U.S. Application Data

[62] Division of Ser. No. 54,811, Jul. 5, 1979, Pat. No. 4,225,508.

[51] Int. Cl.$^3$ .............. C07C 143/72; C07C 149/40; C07C 147/107
[52] U.S. Cl. ...................................... 564/91; 564/95; 564/98; 562/427; 560/10
[58] Field of Search ................... 562/427; 560/10; 260/556 AC; 564/91, 98, 95

[56] References Cited

U.S. PATENT DOCUMENTS

| Re. 30,287 | 5/1980 | Marx et al. | 560/121 X |
| 3,954,741 | 5/1976 | Schaaf et al. | 260/557 R X |
| 4,158,667 | 6/1979 | Axen | 260/413 |
| 4,169,895 | 10/1979 | Hess et al. | 260/556 AC X |
| 4,191,694 | 3/1980 | Skuballa et al. | 260/556 AC X |

FOREIGN PATENT DOCUMENTS 2505519  8/1975  Fed. Rep. of Germany ...... 560/121

Primary Examiner—Winston A. Douglas
Assistant Examiner—Raymond K. Covington
Attorney, Agent, or Firm—L. Ruth Hattan; Robert A. Armitage

[57] ABSTRACT

The present invention provides novel 19-hydroxy-6a-carba-PGI$_2$ sulfonylamides which are useful for pharmacological purposes, e.g., anti-asthmatic indications.

1 Claim, No Drawings

19-HYDROXY-6A-CARBA-PGI₂ SULFONYLAMIDES

DESCRIPTION

Cross Reference to Related Application

The present invention is a divisional application of U.S. Ser. No. 054,811, filed July 5, 1979 now U.S. Pat. No. 4,225,508.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-6a-carba-PGI₂ sulfonlamides. The novel prostacyclin analogs are useful for pharmacological purposes, e.g., as anti-asthmatic agents. The preparation and use of these compounds is incorporated here by reference from U.S. Pat. No. 4,225,508.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI₂, see R. A. Johnson, et al., Prostaglandins 15, 737–740 (1978).

SUMMARY OF THE INVENTION

The present invention particularly provides a prostacyclin-type compound of the formula

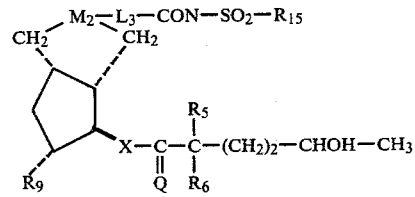

wherein L₃ is
(1) —(CH₂)ₙ—, wherein n is one to 5, inclusive,
(2) —(CH₂)ₚ—CF₂—, wherein p is 2, 3, or 4, or
(3) —CH₂—CH=CH—;
wherein M₂ is

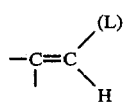 (1)

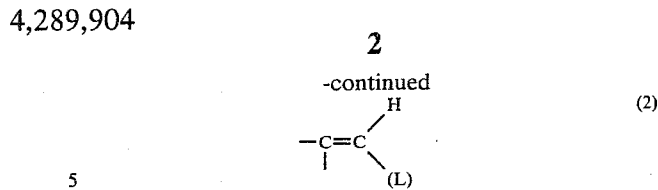 (2)

wherein Q is oxo, α—H:β—H, α—OH:β—R₄, or α—R₄:β—OH, wherein R₄ is hydrogen or alkyl of one to 4 carbon atoms, inclusive, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro; wherein R₁₅ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive; wherein R₉ is hydrogen or hydroxyl; and wherein X is
(1) trans—CH=CH—,
(2) cis—CH=CH—,
(3) —C≡C—, or
(4) —CH₂CH₂—.

I claim:
1. A prostacyclin-type compound of the formula

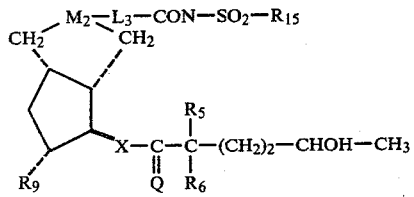

wherein L₃ is
(1) —(CH₂)ₙ—, wherein n is one to 5, inclusive,
(2) —(CH₂)ₚ—CF₂—, wherein p is 2, 3, or 4, or
(3) —CH₂—CH=CH—; wherein M₂ is

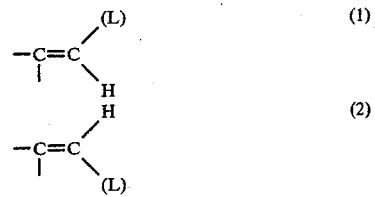 (1)

(2)

wherein Q is oxo, α—H:β—H, α—OH:β—R₄, or α—R₄:β—OH, wherein R₄ is hydrogen or alkyl of one to 4 carbon atoms, inclusive, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro; wherein R₁₅ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive; wherein R₉ is hydrogen or hydroxyl; and wherein X is
(1) trans—CH=CH—,
(2) cis—CH=CH—,
(3) —C≡C—, or
(4) —CH₂CH₂—.

* * * * *